United States Patent
Huebler et al.

(10) Patent No.: US 6,977,083 B1
(45) Date of Patent: Dec. 20, 2005

(54) BIOADHESIVE TABLET CONTAINING TESTOSTERONE/TESTOSTERONE ESTER MIXTURES AND METHOD FOR PRODUCING A PREDETERMINED TESTOSTERONE TIME-RELEASE PROFILE WITH SAME

(75) Inventors: Doris Huebler, Schmieden (DE); Guenter Kaufmann, Jena (DE); Michael Oettel, Jena (DE); Holger Zimmermann, Ilmenau-Roda (DE); Michael Dittgen, Apolda (DE); Sabine Fricke, Jena (DE); Manfred Boese, Jena (DE); Ralf Ladwig, Jena (DE); Sven Claussen, Jena (DE); Carsten Timpe, Weissenborn (DE)

(73) Assignee: Jenapharm GmbH & Co. KG, Jena (DE)

( * ) Notice: Subject to any disclaimer, the term of this patent is extended or adjusted under 35 U.S.C. 154(b) by 0 days.

(21) Appl. No.: 09/806,639

(22) PCT Filed: Sep. 30, 1999

(86) PCT No.: PCT/EP99/07254

§ 371 (c)(1),
(2), (4) Date: May 21, 2001

(87) PCT Pub. No.: WO00/19975

PCT Pub. Date: Apr. 13, 2000

Related U.S. Application Data (60) Provisional application No. 60/105,520, filed on Oct. 26, 1998.

(30) Foreign Application Priority Data

Oct. 2, 1998 (DE) ............................ 198 47 252

(51) Int. Cl.$^7$ ............................................ A61F 13/00
(52) U.S. Cl. ............... 424/434; 424/400; 424/435; 424/444; 424/464; 514/169; 514/772
(58) Field of Search ............... 424/434, 444, 424/464; 514/169, 772

(56) References Cited

U.S. PATENT DOCUMENTS

| 4,396,615 A | 8/1983 | Petrow et al. ............ 424/242 |
| 6,063,404 A * | 5/2000 | Timpe et al. ............ 424/464 |

FOREIGN PATENT DOCUMENTS

| CA | 2 105 887 | 3/1994 |
| EP | 0 286 581 A1 | 10/1988 |
| EP | 0 371 466 A1 | 6/1990 |
| KR | 96-006729 | 5/1996 |
| KR | 9606729 | * 5/1996 |
| WO | 87/04342 | 7/1987 |
| WO | 97 38663 A | 10/1997 |

OTHER PUBLICATIONS

Groening; R., Arzneiformen Mit Elektronisch Gesteuerter Freisetzung, in Pharmazeutische Technologie: Moderne Arzneiformen, S. 441, Aufl., Mueller et al, Wissenschaftliche Verlagsgesellschaft MBH Stuttgar 1998.

Voorspoels, Jody, et al.: "Buccal Absorption of Testosterone . . . ", Pharmaceutical Research Bd. 13, NR. 8, Aug. 1996, pp. 1228-1232.

Wang, Christina, et al: "Testosterone Undecanoate and Testosterone Cyclodextrin", Pharmacology, Biology, and Clinical Applications . . . , Proc. Int. Androg. Workshop, 2nd, 1995, pp. 487-491.

"Die Abhaengigkeit der Grosse und Form der Zeit . . . " by R. Meier and E. Tschopp, in Arch. Exper. Path U. Pharmakol., Bd. 226, pp. 532-546, 1955.(English Translation of the Reference is Enclosed Herewith).

E. Mutschler, Arzneimittelwirkungen, 6. Auflage, pp. 334-337, Wissenschaftliche Verlagsellschaft MBH Stuttgart 1991.
S. G. Johnson, et al: Therapeutic Effectiveness of Oral Testosterone, Lancet, 2., 1974, 1473-1475.
Meier, R., et al: ARch.Exptl. Pathol. Pharmacol. 226, 532 (1955).
A.M. Matsumoto: Hormonal Therapy of Male Hypogonadism. Endocrinol. Metal. Clin. North A. 23, 1994, 857-875.
N.A. Mazer, et al: Enhanced Transdermal Delivery . . . , J. Control. Rel. 19: 347-362, 1992.
Pitha, et al: G-Ciclodextrin: Testosterone Complex Suitable for . . . , J. Pharmaceutical Sciences, 76 (10) 1987, 788-790.
Patent Abstracts of Japan 07118143 A, May 9, 1995.
Auterhoff, H., et al, Lehrbuch der Pharmazeutischen Chemie, 12. Auflage, 570-573, Wissenschaftlische Verlagsgesellschaf mbH Stuttgart 1919.

\* cited by examiner

*Primary Examiner*—Thurman K. Page
*Assistant Examiner*—Lakshmi Channavajjala
(74) *Attorney, Agent, or Firm*—Michael J. Striker (57) ABSTRACT

The method of making a bioadhesive tablet for controlling testosterone blood level, especially in elderly men suffering from partial androgen deficiency, includes spray-drying an alcoholic solution or suspension of testosterone and at least one testosterone ester, preferably in a ratio of 1:10 to 1:1.5, separately or together, with an organic polymer and optionally one or more auxiliary ingredient to form an active ingredient premix. Then various other auxiliary ingredients are mixed, as needed, with the active ingredient premix to form the bioadhesive tablet with an active ingredient layer and an adhesive layer. The active ingredient layer contains an effective amount of the active ingredient premix. The adhesive layer includes auxiliary ingredients including the bioadhesive polymer. The bioadhesive tablet may be buccally administered to provide a predetermined timed release profile of testosterone, advantageously varying according to a circadian rhythm.

15 Claims, 3 Drawing Sheets

BIOADHESIVE TABLET CONTAINING TESTOSTERONE/TESTOSTERONE ESTER MIXTURES AND METHOD FOR PRODUCING A PREDETERMINED TESTOSTERONE TIME-RELEASE PROFILE WITH SAME

This claims the benefit of Provisional Application No. 60/105,520, filed Oct. 26, 1998.

BACKGROUND OF THE INVENTION

1. Field of the Invention

The invention relates to a combination of testosterone and testosterone esters (or to the sole use of testosterone esters) in a buccal, bioadhesive preparation so that, by finely adjusted dosing of the active ingredients and ester selection, various desired plasma levels of testosterone can be set or produced in individual patients, for example to restore an endogenous body rhythm.

2. Description of the Related Art

Testosterone is quantitatively and qualitatively the most important androgen synthesized in the body. It is formed mainly in the testicles and in small amounts in the adrenal glands and in women in the ovaries. In males, testosterone is responsible for the development of the male characteristics during fetal, neonatal and pubertal maturation and finally for attaining the male phenotype and for androgen-dependent functions (for example spermatogenesis). Testosterone exerts protein-anabolic action (in muscles, bones, hematopoiesis, kidneys and liver) {E. Mutschler, "Arzneimittelwirkungen" [Drug Actions], 6th edition, pp. 334–337, Wissenschaftliche Verlagsgesellschaft mbh [publisher], Stuttgart, 1991}.

After oral or parenteral administration, testosterone is rapidly absorbed in the gastrointestinal tract. It is then transported by the portal vein to the liver where it is rapidly metabolized. As a result, the plasma half-life of testosterone is short, i.e., about 10 minutes {Auterhoff, H., Knabe, J. and Höltje, H. D., "Lehrbuch der Pharmazeutischen Chemie" [Textbook of Pharmaceutical Chemistry], 12th edition, pp. 570–573, Wissenschaftliche Verlagsgesellschaft mbh [publisher], Stuttgart, 1991}. To develop a physiological serum level, oral administration of 400 mg (!) of testosterone is needed (S. G. Johnson, E. P. Bennet and V. G. Jensen, Therapeutic effectiveness of oral testosterone, Lancet 2:1974, 1473–1475).

To prolong the action of testosterone, testosterone esters with varying chain length (testosterone propionate, testosterone enantate, testosterone undecanoate) are injected intramuscularly as an oily solution or suspension. It is known that in contact with body fluids these esters will slowly hydrolyze under the action of esterases thus releasing the pharmacologically active testosterone. The influence of the type of ester on the growth of the capon comb after i.m. injection has already been described (Meier, R. and Tschopp, E., Arch. Exptl. Pathol. Pharmacol. 226:1955, 532).

Moreover, testosterone undecanoate (in oleic acid, as a soft gelatin capsule) is administered orally via the lymphatic route [Andriol® preparation]. From the oleic acid-embedded preparation, the drug passes from the gastrointestinal tract through the thoracic duct into the lymph tract thus reaching the systemic circulation. This gives rise to varying serum levels and gastrointestinal side effects. These effects can make long-term replacement therapy difficult (A. M. Matsumoto: Hormonal therapy of male hypogonadism, Endocrinol. Metab. Clin. North Am. 23:1994, 857–875).

Other routes of administration (transdermal, nasal, sublingual, buccal, subcutaneous) have been studied by various research groups (for example, by N. A. Mazer, W. E. Heiber, J. F. Moellmer, A. W. Meikle, J. D. Stringham, S. W. Sanders, K. G. Tolman and W. D. Odell, Enhanced transdermal delivery of testosterone: A new physiological approach for androgen replacement in hypogonadal men, J. Controll. Rel. 19:1992, 347–362).

Drawbacks of the aforesaid therapies are: 1. either a too short, rapidly decreasing testosterone level (after oral administration) or 2.—in the case of intramuscular injection of testosterone esters—the fact that a constantly set testosterone level cannot be changed over a long period of time (days to weeks) thus not allowing individual time control of the testosterone action. Moreover, down regulation of the basal testosterone secretion can take place.

The low bioavailability caused by the high first-pass effect in the liver can be circumvented by buccal or sublingual administration. Various studies confirm this (for example, Pitha, J., Anaissie, J. and Uekama, K., g-Cyclodextrin: Testosterone complex suitable for sublingual administration, J. Pharmaceutical Sciences 76 (10):1987, 788–790).

Buccal administration of drugs is known from the prior art.

EP-0371466 A concerns a rapidly soluble tablet for fast buccal administration of steroids, among other things (for example estrogens, progestins). The main ingredient used is a water-soluble polyhydric alcohol, particularly sorbitol. The advantage is a rapid initial increase in drug concentration.

EP-0286581 A discloses the transmucosal buccal administration of estrogens (17β-estradiol and ethinylestradiol). The estrogen is used within the framework of hormone replacement therapy in postmenopausal women for treating PMS (postmenopausal syndrome) and for osteoporosis therapy at a dose of 50–100 μg/day (17β-estradiol for PMS therapy) and at a dose of 200–400 μg/day (17β-estradiol for osteoporosis therapy). Buccal administration makes it possible to attain therapeutic plasma levels by circumventing the first-pass effect.

WO-704342 describes a special formulation said to be particularly suitable for, among other things, the buccal administration of estrogens (for example estradiol and the esters of estradiol), progestins, androgens and anabolic steroids. This formulation contains a) about 1–20% of a soluble, adhesive polymer (carbomers, partly hydrolyzed polyvinyl alcohol [PVA], polyethylene oxide, polyacrylate, hydroxypropylmethylcellulose), b) a soluble, directly tabletted auxiliary agent and c) the active ingredient. The adhesive polymer makes the formulation or drug form adhere at the site of administration.

U.S. Pat. No. 4,396,615-A describes the treatment of androgen-related diseases by administration of 6-methylene-progesterone, a testosterone-5α-reductase inhibitor, in the form of topical formulations. Such formulations contain the inhibitor and an inert topical carrier (for example, a silicone, methylcellulose, hydroxymethylcellulose).

CA-2105887-A discloses a bioerodable system for buccal and vaginal administration of hormones (estradiol), among other things. The system is water-soluble and mucoadherent. It consists of a solid, soluble, lyophilized foam and the active ingredient. The disintegration time is at least 8 hours. The system adheres to the mucosal membrane where it releases the drug. The polymers used are primarily gelatin, sodium carboxymethylcellulose, methylcellulose etc. A particular advantage of the system is its long adhesion time.

As regards the tailored time-release control of drugs, note that it is not possible for our currently available drugs to provide variable release of the active ingredient nor to adapt the release to the drug needs of an individual patient.

For release-control purposes, current depot drugs use passive dissolution, diffusion, swelling and erosion processes {Gröning, R., "Arzneiformen mit elektronisch gesteuerter Freisetzung" [Drug Forms with Electronically Controlled Release], in "Pharmazeutische Technologie: Moderne Arzneiformen" [Pharmaceutical Technology: Modern Drug Forms], p. 441, ed. [sic-Translator], Müller R. H. and Hildebrand, G. E. (editors), Wissenschaftliche Verlagsgesellschaft mbh [publisher], Stuttgart, 1998}.

The time-controlled release of drugs is also known from the prior art.

JP-07118143 discloses time-controlled capsules which a) are water-insoluble or partly water-soluble, b) consist of water-swellable substances (powder, granulates or pills of, for example, calcium carboxy-methylcellulose or polyvinylpyrrolidone) and c) contain elements (tablets) with the active ingredient in the center of the capsule.

The prior art also describes sustained-release preparations using polymers. Thus EP-068446, for example, discloses the use of methylcellulose or carboxymethylcellulose in sustained-release mixtures.

SUMMARY OF THE INVENTION

The object of the present invention is to make use of the advantages of buccal administration of steroids with high first-pass effect and low bioavailability, especially of testosterone and the esters thereof, by exploiting the different pharmacokinetics of the various testosterone esters (depending on chain length), so as to be able, by careful selection of appropriate dosages and esters, to attain a desired drug profile.

This objective is reached by use of testosterone esters with 1 to 20 carbon atoms in the carboxylic acid radical or of a mixture of two or more testosterone esters with different carboxylic acid radicals and/or testosterone, for the preparation of buccally administered bioadhesive systems with time-controlled release of the active ingredient, for treating diseases associated with a modified testosterone level.

Preferably used are testosterone esters wherein the carbon structure of the carboxylic acid radical is linear, branched, alicyclic, saturated and/or unsaturated and contains up to five double and/or triple bonds.

Also preferred is a ratio of testosterone to testosterone ester from 1:100 to 1:1 and particularly from 1:10 to 1:1.5.

It is particularly preferred that the buccally administered bioadhesive systems be prepared by first embedding into an organic polymer the active ingredients, separately or together, in an amorphous state as obtained by use of a spray-drying process.

It is especially preferred to mix the amorphous, spray-dried testosterone products with other auxiliary agents, binders, fillers, lubricants, bioadhesive polymers, surfactants or disintegration accelerators and to compress the mixture into single-layer or multilayer tablets.

The use for a tailored adjustment of therapeutic and/or circadian rhythms of the testosterone levels is preferred.

Surprisingly, we have now found that the chain length of the testosterone ester not only determines the solubility, but, as was shown experimentally, evidently also the kinetics of ester cleavage in the blood or tissue fluids by the corresponding hydrolases. Note in particular, when testosterone esters are employed, the use of the embedding technique of spray-drying in organic polymers (polyvinylpyrrolidone, hydroxypropylmethylcellulose, solid polyethylene glycols) to achieve improved solubility in the oral cavity. This is particularly important in view of the small saliva volumes (about 1–1.5 mL) which here, on the average, are available for the dissolution of sparingly soluble esters. In the publication by Jody Voorspoels [Vorspoels, J., Remon, J. P., Eechaute, W. E. and De Sy, W., Buccal Absorption of Testosterone and Its Esters Using a Bioadhesive Tablet in Dogs, Pharmaceutical Research, vol. 13, No. 8, 1996, 1228–1232), the testosterone esters (testosterone acetate, testosterone propionate, testosterone enantate, testosterone decanoate) studied in six castrated beagle dogs did not show a higher bioavailability than testosterone in spite of their higher lipophilicity. Because the esters were directly compressed only after dry mixing, without using a special premixing technology (amorphization by spray-drying), these poorer results presumably are due to the low, and in some cases extremely low, solubility of the esters in the crystalline state.

We were able to show that by the use of buccal administration of testosterone in combination with testosterone esters of different chain length, it is possible to attain different blood level patterns or rhythms (such as a circadian rhythm). In selecting the testosterone ester, the choice can be made specifically from three groups: 1. esters of shorter chain length (for example, testosterone acetate or propionate), 2. esters of medium chain length (for example testosterone enantate, cipionate or cyclohexanecarboxylate) and 3. esters of higher chain length (for example testosterone undecanoate, or bucyclate).

According to the invention, this objective is reached by dissolving testosterone or the particular testosterone ester together with the polymer (for example polyvinylpyrrolidone or hydroxypropyl-methylcellulose) in ethanol and processing the mixtures further in a spray-drying unit to form an amorphous, embedded, spray-dried formulation. It is possible in this case 1) to embed said active ingredients separately from each other or 2) to embed them together in a single processing step, to obtain an amorphous mixture.

The fine-particle embedded spray-dried material is then subjected to dry mixing with other auxiliary agents for making bioadhesive buccal tablets [binders: polyvinylpyrrolidone, cellulose ethers; fillers: Cellactose®, mannitol, sorbitol, lactose; lubricants: magnesium stearate, hydrogenated vegetable fats; bioadhesive polymers: polyacrylates (Carbopols®, sodium carboxymethylcellulose) and optionally other auxiliary agents, such as surfactants or disintegration accelerators]. The mixture is then compressed into buccal tablets which can have a layered structure (active ingredient layer, bioadhesive layer; unidirectional or multidirectional release).

Based on blood level studies with the individual drug components alone, it is possible to attain the appropriate release patterns by changing the following two parameters
dosage of the active ingredient
selection of the ester or of the chain length at C-17.

An advantageous combination is, for example, that of the short-acting testosterone with testosterone undecanoate (eleven-carbon chain) which has a longer half-life (see practical examples).

To this end, an advantageous ratio of the active ingredients, namely of testosterone to Σ testosterone esters, is from 1:100 to 1:1 and particularly from 1:10 to 1:1.5.

By skillful combination of testosterone with testosterone esters, it is possible to attain blood level patterns which are capable of recreating or simulating the body's own rhythmicity of endogenous testosterone levels. For example, the duration of action of a bioadhesive buccal tablet with testosterone can be prolonged by combining testosterone with testosterone undecanoate (cf. FIG. 1 and FIG. 3). In the practical example (equimolar combination), the duration of blood levels of >100 ng/mL is increased in female dogs from 2 to 4 hours. Moreover, a marked (slower) pulse is reached with a maximum appearing after about 3 hours. After 8 h, the testosterone values of nearly 50 ng/mL are still double as high as those attained with testosterone alone.

In essence, the set blood level pattern of testosterone is controlled through two parameters:

The chain length and steric structure of the ester chain at C-17. This structure determines, on the one hand, the lipophilicity and thus the solubility and, on the other, in a pronounced manner, the rate of ester cleavage and hydrolysis (interactions of the ester side chain with the active center of hydrolases). For example, esters with a longer chain length are cleaved more slowly than those with an intermediate or shorter chain length. In this sense, the released testosterone becomes available more slowly than after administration of pure testosterone, i.e. the peak appears later. Through the chain length, it is thus possible to attain a more or less tailored time control of therapeutic action.

The dosage of testosterone or of the testosterone esters on the basis of direct proportionality between the area under the curve [AUC] and the dose given.

This could be important for hormone replacement therapy in elderly men with partial androgen deficiency (PADAM patients) in that a deficient plasma level could be appropriately corrected.

BRIEF DESCRIPTION OF THE SEVERAL VIEWS OF THE DRAWING

The objects, features and advantages of the invention will now be illustrated in more detail with the aid of the following description of the preferred embodiments, with reference to the accompanying figures in which.

The following practical examples illustrate the invention without limiting its scope.

| Bioadhesive Tablet with Testosterone | |
|---|---|
| Formulation Component | Weight/tablet |
| Active ingredient layer | |
| Testosterone premix (20%) | 50.00 |
| Mannitol | 43.90 |
| Cellactose 80 | 29.50 |
| Carmellose sodium | 1.20 |
| Magnesium stearate | 1.50 |
| Talc | 4.50 |

| -continued | |
|---|---|
| Bioadhesive Tablet with Testosterone | |
| Formulation Component | Weight/tablet |
| Adhesive layer | |
| Mannitol | 17.40 |
| Cellactose 80 | 34.82 |
| Carmellose sodium | 10.18 |
| Magnesium stearate | 0.65 |
| Red iron oxide | 0.05 |
| Talc | 1.90 |

Preparation:

Preparation of the Premix

The testosterone premix (20%) was prepared by spray-drying. To this end, the active ingredient together with the polymer (for example, polyvinylpyrrolidone, hydroxypropylmethylcellulose) and optionally another auxiliary agent (carrier or antistatic agent) were dissolved or suspended in an appropriate solvent. The homogenized suspension obtained by steady stirring was spray-dried in a spray-drying unit to obtain a fine powder.

Preparation of the Active Ingredient Layer

This premix was mixed with the other auxiliary agents for the active ingredient layer (mannitol, Cellactose 80) in an appropriate mixer (type: Kubu mixer, Turbula mixer, tumble mixer etc) for about 20 minutes. The outer phase (Carmellose sodium, magnesium stearate, talc) was then added, and mixing was continued for 5 minutes.

Preparation of the Adhesive Layer

Red iron oxide and talc were intimately ground in a ball mill. In an appropriate mixer (type: Kubu mixer, Turbula mixer, tumble mixer etc), mannitol and Cellactose 80 were mixed for about 20 min. The ground colored mixture, Carmellose sodium and magnesium stearate were then added as the outer phase, and mixing was continued for an additional 5 minutes.

The mixtures for the active ingredient layer and adhesive layer, in the weight ratio given, were then compressed in an appropriate tabletting press to form two-layer tablets.

Figure 1:
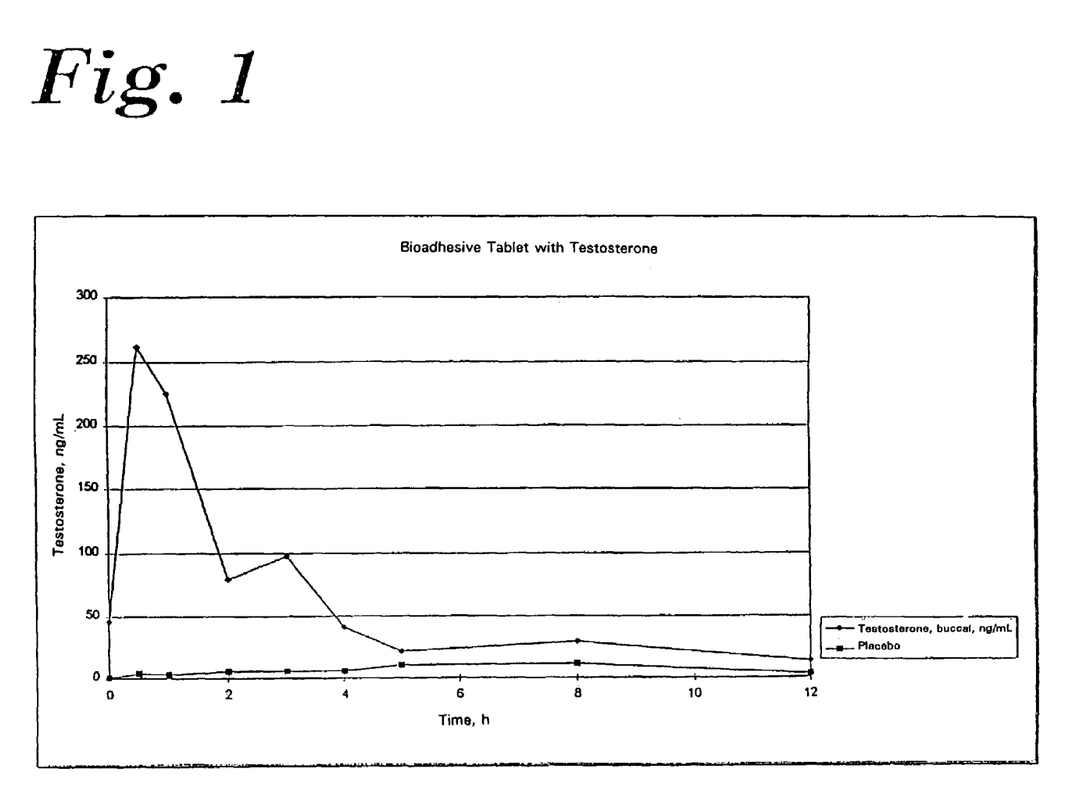
FIG. 1 is a graphical illustration showing a testosterone concentration profile produced by administration of testosterone alone.

FIG. 1 shows the blood level variation for a formulation according to Example 1.

| Bioadhesive Tablet with Testosterone Undecanoate | |
|---|---|
| Formulation Component | Weight/tablet |
| Active ingredient layer | |
| Testosterone undecanoate premix (20%) | 50.00 |
| Mannitol | 43.90 |
| Cellactose 80 | 29.50 |
| Carmellose sodium | 1.20 |
| Magnesium stearate | 1.50 |
| Talc | 4.30 |
| Adhesive layer | |
| Mannitol | 17.40 |
| Cellactose 80 | 34.82 |
| Carmellose sodium | 10.18 |
| Magnesium stearate | 0.65 |

-continued

| Bioadhesive Tablet with Testosterone Undecanoate | |
|---|---|
| Formulation Component | Weight/tablet |
| Red iron oxide | 0.05 |
| Talc | 1.90 |

Preparation:

Preparation of the Premix

The testosterone undecanoate premix (20%) was prepared by spray-drying. To this end, the active ingredient together with the polymer (for example, polyvinylpyrrolidone, hydroxypropylmethylcellulose) and optionally another auxiliary agent (carrier or antistatic agent) were dissolved or suspended in an appropriate solvent. The homogenized suspension obtained by steady stirring was spray-dried in a spray-drying unit to obtain a fine powder.

Preparation of the Active Ingredient Layer

This premix was mixed with other auxiliary agents for the active ingredient layer (mannitol, Cellactose 80) in an appropriate mixer (type: Kubu mixer, Turbula mixer, tumble mixer etc) for about 20 minutes. The outer phase (Carmellose sodium, magnesium stearate, talc) was then added, and mixing was continued for 5 minutes.

Preparation of the Adhesive Layer

Red iron oxide and talc were intimately ground in a ball mill. In an appropriate mixer (type: Kubu mixer, Turbula mixer, tumble mixer etc), mannitol and Cellalactose 80 were mixed for about 20 min. The ground colored mixture, Carmellose sodium and magnesium stearate were then added as the outer phase, and mixing was continued for an additional 5 minutes.

The mixtures for the active ingredient layer and adhesive layer, in the weight ratio given, were then compressed in an appropriate tabletting press to obtain two-layer tablets.

Figure 2:
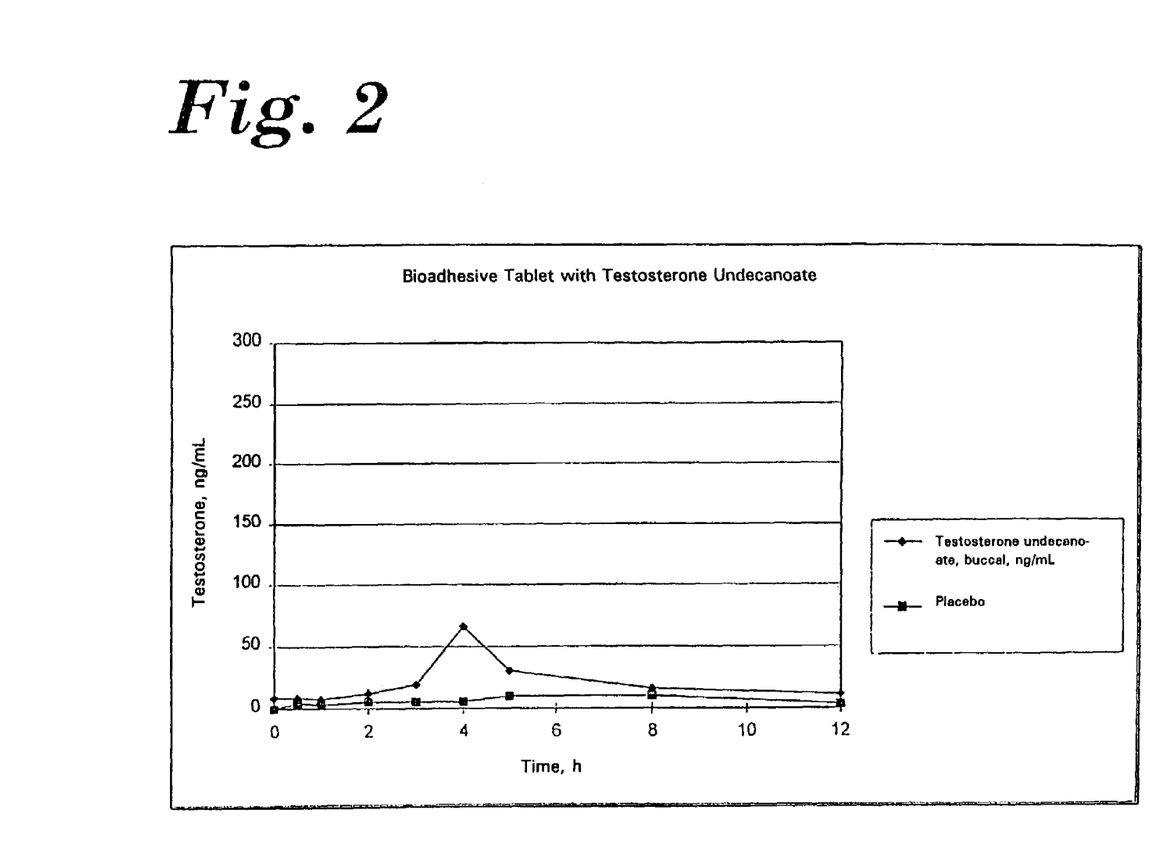
FIG. 2 is a graphical illustration showing a testosterone concentration profile produced by buccal administration of a bioadhesive tablet containing testosterone undeconate alone.

FIG. 2 shows the blood level variation for a formulation according to Example 2

| Bioadhesive Tablet with Testosterone and Testosterone Undecanoate | |
|---|---|
| Formulation Component | Weight/tablet |
| Active ingredient layer | |
| Testosterone/ testosterone undecanoate premix (20%, 20%) | 50.00 |
| Mannitol | 43.90 |
| Cellactose 80 | 29.50 |
| Carmellose sodium | 1.20 |
| Magnesium stearate | 1.50 |
| Talc | 4.30 |
| Adhesive layer | |
| Mannitol | 17.40 |
| Cellactose 80 | 34.82 |
| Carmellose sodium | 10.18 |
| Magnesium stearate | 0.65 |
| Red iron oxide | 0.05 |
| Talc | 1.90 |

Preparation of the Premix

The testosterone/testosterone undecanoate premix (20%) was prepared by spray-drying. To this end, the active ingredient together with the polymer (for example, polyvinylpyrrolidone, hydroxypropylmethylcellulose) and optionally another auxiliary agent (carrier or antistatic agent) were dissolved or suspended in an appropriate solvent. The homogenized suspension obtained by steady stirring was spray-dried in a spray-drying unit to obtain a fine powder.

Preparation of the Active Ingredient Layer

This premix was mixed with other auxiliary agents for the active ingredient layer (mannitol, Cellactose 80) in an appropriate mixer (type: Kubu mixer, Turbula mixer, tumble mixer etc) for about 20 minutes. The outer phase (Carmellose sodium, magnesium stearate, talc) was then added, and mixing was continued for 5 minutes.

Preparation of the Adhesive Layer

Red iron oxide and talc were intimately ground in a ball mill. In an appropriate mixer (type: Kubu mixer, Turbula mixer, tumble mixer etc), mannitol and Cellalactose 80 were mixed for about 20 min. The ground colored mixture, Carmellose sodium and magnesium stearate were then added as the outer phase, and mixing was continued for an additional 5 minutes.

The mixtures for the active ingredient layer and adhesive layer, in the weight ratio given, were then compressed in an appropriate tabletting press to form two-layer tablets.

Figure 3:
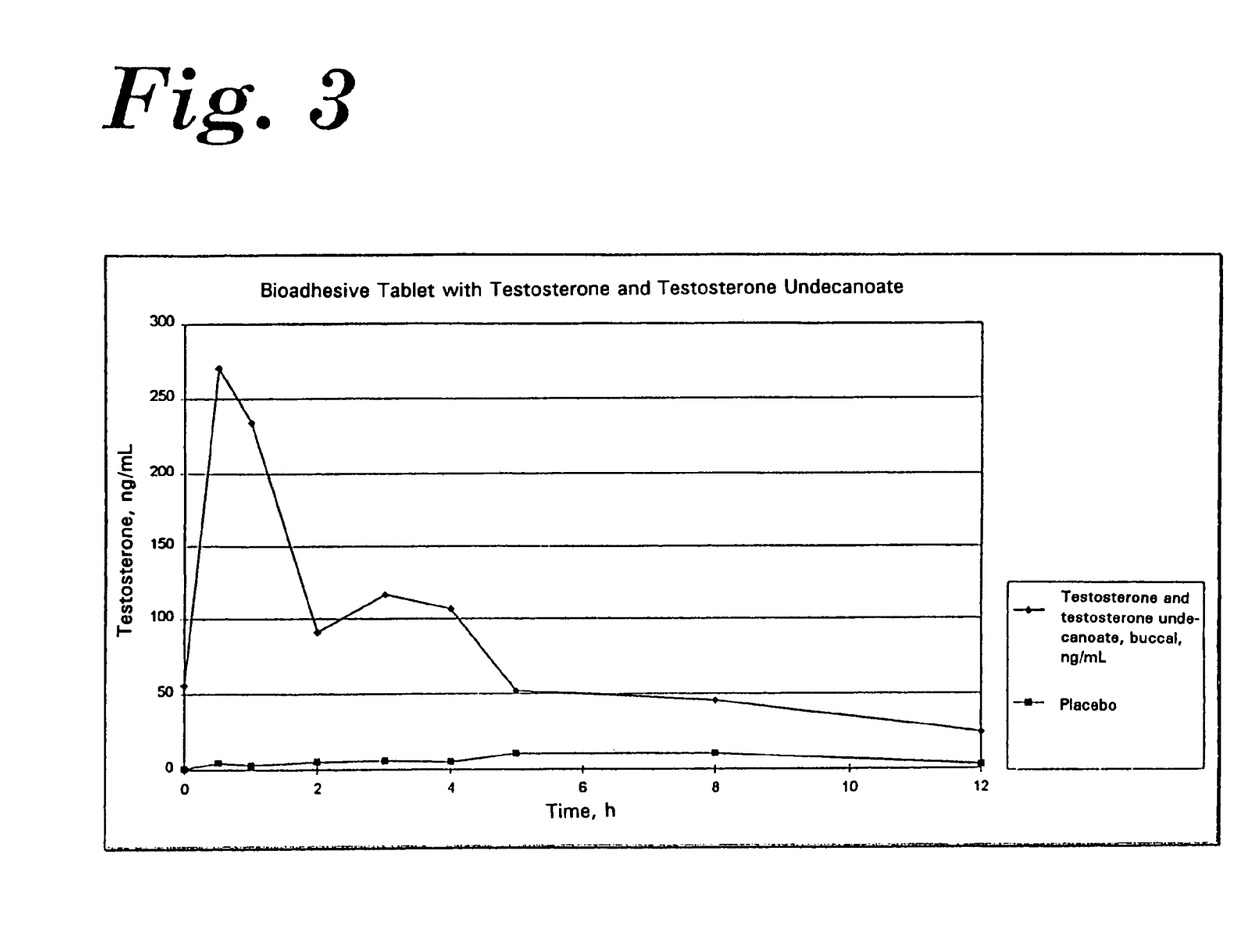
FIG. 3 is a graphical illustration showing a testosterone concentration profile produced by buccal administration of a bioadhesive tablet according to the invention containing a mixture of testosterone and testosterone undeconate in a 1:1 ratio.

FIG. 3 shows the blood level variation for a formulation according to Example 3.

| Bioadhesive Tablet with Testosterone and Testosterone Enantate | |
|---|---|
| Formulation Component | Weight/tablet |
| Active ingredient layer | |
| Testosterone/ testosterone enantate premix (20%, 20%) | 50.00 |
| Mannitol | 58.60 |
| Emcompress | 14.00 |
| Carbopol ® 974 | 2.00 |
| Magnesium stearate | 1.50 |
| Talc | 4.30 |
| Adhesive layer | |
| Mannitol | 17.40 |
| Emcompress | 34.82 |
| Carbopol ® 974 | 13.00 |
| Magnesium stearate | 0.65 |
| Red iron oxide | 0.05 |
| Talc | 1.90 |

Preparation:

Preparation of the Premix

The testosterone/testosterone enantate premix (20%) was prepared by spray-drying. To this end, the active ingredient together with the polymer (for example, polyvinylpyrrolidone, hydroxypropylmethylcellulose and optionally another auxiliary agent (carrier or antistatic agent) were dissolved or suspended in an appropriate solvent. The homogenized suspension obtained by steady stirring was spray-dried in a spray-drying unit to form a fine powder.

Preparation of the Active Ingredient Layer

This premix was mixed with other auxiliary agents for the active ingredient layer (mannitol, Emcompress) in an appropriate mixer (type: Kubu mixer, Turbula mixer, tumble mixer etc) for about 20 minutes. The outer phase (Carbopol® 974, magnesium stearate, talc) was then added, and mixing was continued for 5 minutes.

Preparation of the Adhesive Layer

Red iron oxide and talc were intimately ground in a ball mill. In an appropriate mixer (type: Kubu mixer, Turbula mixer, tumble mixer etc), mannitol and Emcompress were mixed for about 20 min. The ground colored mixture, Carbopol® 974 and magnesium stearate were then added as the outer phase, and mixing was continued for an additional 5 minutes. The mixtures for the active ingredient layer and adhesive layer, in the weight ratio given, were then compressed in an appropriate tabletting press to form two-layer tablets.

Bioadhesive Tablet with Testosterone Propionate and Testosterone Undecanoate

| Formulation Component | Weight/tablet |
|---|---|
| Active ingredient layer | |
| Testosterone propionate/ testosterone enantate premix (20%, 20%) | 50.00 |
| Mannitol | 58.60 |
| Emcompress | 14.00 |
| Carbopol ® 974 | 2.00 |
| Magnesium stearate | 1.50 |
| Talc | 4.30 |
| Adhesive layer | |
| Mannitol | 17.40 |
| Emcompress | 34.82 |
| Carbopol ® 974 | 13.00 |
| Magnesium stearate | 0.65 |
| Red iron oxide | 0.05 |
| Talc | 1.90 |

Preparation:

Preparation of the Premix

The testosterone propionate/testosterone undecanoate premix (20%) was prepared by spray-drying. To this end, the active ingredient together with the polymer (for example, polyvinylpyrrolidone, hydroxypropylmethylcellulose) and optionally another auxiliary agent (carrier or antistatic agent) were dissolved or suspended in an appropriate solvent. The homogenized suspension obtained by steady stirring was spray-dried in a spray-drying unit to obtain a fine powder.

Preparation of the Active Ingredient Layer

This premix was mixed with other auxiliary agents for the active ingredient layer (mannitol, Emcompress) in an appropriate mixer (type: Kubu mixer, Turbula mixer, tumble mixer etc) for about 20 minutes. The outer phase (Carbopol® 974, magnesium stearate, talc) was then added, and mixing was continued for 5 minutes.

Preparation of the Adhesive Layer

Red iron oxide and talc were intimately ground in a ball mill. In an appropriate mixer (type: Kubu mixer, Turbula mixer, tumble mixer etc), mannitol and Emcompress were mixed for about 20 min. The ground colored mixture, Carbopol® 974 and magnesium stearate were then added as the outer phase, and mixing was continued for an additional 5 minutes.

The mixtures for the active ingredient layer and adhesive layer, in the weight ratio given, were then compressed in an appropriate tabletting press to form two-layer tablets.

What is claimed is:

1. A method of manufacturing a bioadhesive tablet for controlling testosterone blood level in a person for therapeutic purposes, said method comprising embedding testosterone undecanoate alone or a mixture of testosterone undecanoate and testosterone in an organic polymer, hydroxypropymethyl cellulose optionally together with at least one auxiliary agent, by a spray-drying process, so as to form an amorphous active ingredient premix.

2. The method as defined in claim 1, wherein said amorphous active ingredient premix comprises said mixture of said testosterone undecanoate and said testosterone in a ratio of said testosterone to said testosterone undecanoate of from 1:100 to 1:1.

3. The method as defined in claim 2, wherein said ratio is from 1:10 to 1:1.5.

4. A method of manufacturing a bioadhesive tablet for controlling testosterone blood level in a person for therapeutic purposes, said method comprising embedding a mixture of testosterone and testosterone undecanoate in an hydroxypropylmethyl cellulose in a ratio of 1:10 to 1:1.5, optionally together with at least one auxiliary agent, by a spray-drying process, so as to form an amorphous active ingredient premix;

wherein said spray-drying process comprises spray-drying a solution of said hydroxylpropylmethyl, said testosterone and said testosterone undecanoate ester and optionally said at least one auxiliary agent in a solvent.

5. The method as defined in claim 1 or 4, further comprising mixing said amorphous active ingredient premix with at least one auxiliary ingredient to form a mixture and compressing said mixture to form said bioadhesive tablet.

6. The method as defined in claim 1, further comprising mixing said amorphous active ingredient premix with at least one auxiliary ingredient to form an active ingredient layer mixture, preparing an adhesive layer mixture and compressing the active ingredient layer mixture together with the adhesive layer mixture to form said bioadhesive tablet with a bi-layer structure.

7. The method as defined in claim 6, wherein said at least one auxiliary ingredient is selected from the group consisting of binders, fillers, lubricants, surfactants and a disintegration accelerator and said adhesive layer mixture comprises a bioadhesive polymer.

8. The method as defined in claim 1 or 4, further comprising mixing said amorphous active ingredient premix with at least one auxiliary ingredient to form an active ingredient layer mixture, preparing at least one other layer mixture including an adhesive layer mixture and compressing the active ingredient layer mixture together with the at least one other layer mixture to form said bioadhesive tablet with a multi-layer structure.

9. A bioadhesive tablet for controlling testosterone blood level in a person for therapeutic purposes, said bioadhesive tablet being made by a method comprising embedding testosterone undecanoate alone or a mixture of testosterone undecanoate and testosterone in hydroxypropylmethyl cellulose, optionally together with at least one auxiliary agent, by a spray-drying process, so as to form an amorphous active ingredient premix.

10. The tablet as defined in claim 9, wherein said amorphous active ingredient premix comprises said mixture of said testosterone undecanoate and said testosterone in a ratio of said testosterone to said testosterone undecanoate of from 1:100 to 1:1.

11. The tablet as defined in claim 10, wherein said ratio is from 1:10 to 1:1.5.

12. A bioadhesive tablet for controlling testosterone blood level in a person for therapeutic purposes, said bioadhesive tablet being made by a method comprising embedding a mixture of testosterone and testosterone undecanoate in a ratio of 1:10 to 1:1.5 in hydroxypropylmethyl cellulose, optionally together with at least one auxiliary agent, by a spray-drying process, so as to form an amorphous active ingredient premix;

wherein said spray-drying process comprises spray-drying a solution of said organic polymer, said testosterone and said testosterone undecanoate ester and optionally said at least one auxiliary agent in a solvent.

13. The tablet as defined in claim 12, wherein said method comprises mixing said amorphous active ingredient premix with at least one auxiliary ingredient to form a mixture and compressing said mixture to form said bioadhesive tablet.

14. The tablet as defined in claim 12, wherein said method comprises mixing said amorphous active ingredient premix with at least one auxiliary ingredient to form an active ingredient layer mixture, preparing an adhesive layer mixture and compressing the active ingredient layer mixture together with the adhesive layer mixture to form said bioadhesive tablet with a bi-layer structure.

15. The tablet as defined in claim 12, wherein said method comprises mixing said amorphous active ingredient premix with at least one auxiliary ingredient to form an active ingredient layer mixture, preparing at least one other layer mixture including an adhesive layer mixture and compressing the active ingredient layer mixture together with the at least one other layer mixture to form said bioadhesive tablet with a multi-layer structure.

* * * * *